(12) United States Patent
Porath et al.

(10) Patent No.: US 7,996,059 B2
(45) Date of Patent: Aug. 9, 2011

(54) ESOPHAGUS IMAGING ENHANCEMENT DEVICE

(75) Inventors: Joshua Porath, Haifa (IL); Yitzhack Schwartz, Haifa (IL)

(73) Assignee: Biosense Webster, Inc., Diamond Bar, CA (US)

( * ) Notice: Subject to any disclaimer, the term of this patent is extended or adjusted under 35 U.S.C. 154(b) by 830 days.

(21) Appl. No.: 11/370,666

(22) Filed: Mar. 8, 2006

(65) Prior Publication Data

US 2007/0225593 A1   Sep. 27, 2007

(51) Int. Cl.
*A61B 5/05* (2006.01)
*A61B 18/04* (2006.01)
*A61H 1/00* (2006.01)

(52) U.S. Cl. ............ 600/424; 600/425; 600/427; 601/2; 606/32

(58) Field of Classification Search .................. 600/424, 600/470, 425–427; 601/1, 2; 623/1.12, 1.11; 382/128; 606/32
See application file for complete search history.

(56) References Cited

U.S. PATENT DOCUMENTS

| | | | |
|---|---|---|---|
| 5,117,828 A | | 6/1992 | Metzger et al. |
| 5,391,199 A | * | 2/1995 | Ben-Haim ............ 607/122 |
| 5,443,489 A | | 8/1995 | Ben-Haim |
| 5,624,450 A | * | 4/1997 | Glastra ............ 606/108 |
| 5,746,717 A | * | 5/1998 | Aigner ............ 604/102.03 |
| 5,928,248 A | * | 7/1999 | Acker ............ 623/1.11 |
| 5,944,022 A | | 8/1999 | Nardella et al. |
| 5,967,977 A | * | 10/1999 | Mullis et al. ............ 600/380 |
| 5,983,126 A | | 11/1999 | Wittkampf |
| 6,239,724 B1 | | 5/2001 | Doron et al. |
| 6,332,089 B1 | | 12/2001 | Acker et al. |
| 6,456,864 B1 | | 9/2002 | Swanson et al. |
| 6,618,612 B1 | | 9/2003 | Acker et al. |
| 6,690,963 B2 | | 2/2004 | Ben-Haim et al. |
| 7,406,346 B2 | | 7/2008 | Kleen et al. |
| 2002/0065455 A1 | | 5/2002 | Ben-Haim et al. |
| 2002/0077552 A1 | * | 6/2002 | Edwardsen et al. ........ 600/463 |
| 2003/0120150 A1 | | 6/2003 | Govari |
| 2004/0068178 A1 | | 4/2004 | Govari |
| 2004/0078036 A1 | | 4/2004 | Keidar |
| 2004/0147920 A1 | | 7/2004 | Keidar |
| 2005/0010278 A1 | * | 1/2005 | Vardi et al. ............ 623/1.15 |
| 2006/0106375 A1 | * | 5/2006 | Werneth et al. ............ 606/32 |

FOREIGN PATENT DOCUMENTS

| | | |
|---|---|---|
| CN | 1572248 A | 2/2005 |
| CN | 1700880 A | 11/2005 |
| WO | WO 96/05768 A1 | 2/1996 |
| WO | WO 03/030713 A2 | 4/2003 |

OTHER PUBLICATIONS

Biosense Webster, Inc., U.S. Appl. No. 11/030,934—pending.

(Continued)

*Primary Examiner* — Long V Le
*Assistant Examiner* — Katherine L Fernandez
(74) *Attorney, Agent, or Firm* — Louis J. Capezzuto

(57) ABSTRACT

A device for enhancing visualization of an esophagus when imaged by a visualization system includes a structure including material that is clearly visible when imaged by the visualization system. The structure is arranged, when inserted into the esophagus, to expand so as to conform to an inner surface of the esophagus in order to enhance a visualization quality of the surface when imaged by the visualization system. A cord attached to the structure is arranged to extend out of the esophagus so as to assist a removal of the device from the esophagus.

26 Claims, 3 Drawing Sheets

OTHER PUBLICATIONS

Biosense Webster, Inc., U.S. Appl. No. 11/195,050—pending.

Biosense Webster, Inc., U.S. Appl. No. 11/195,123—pending.

Cury, R.C. et al., "The Relationship of the Esophagus and Aorta to the Left Atrium and Pulmonary veins: Implications for Catheter Ablation of Atrial Fibrillation", This work was supported in part by an NIH K23 award (HL68064-02) to Dr. Reddy. Unedited Manuscript, pp. 1-18.

Kottkamp, H. M.D. et al., "Topographic Variability of the Esophageal Left Atrial Relation Influencing Ablation Lines in Patients with Atrial Fibrillation", J Cardiovasc Electrophysiol, vol. 16, pp. 1-5, Apr. 2005.

Lemola, K. M.D. et al., "Computed Tomographic Analysis of the Anatomy of the Left Atrium and the Esophagus Implications for Left Atrial Catheter Ablation", Circulation, 2004;110:3655-3660.

Pollak, S.J., M.C. et al., "Novel Imaging Techniques of the Esophagus Enhancing Safety of Left Atrial Ablation", J Cardiovasc Electrophysiol, vol. 16, pp. 1-5, Mar. 2005.

Redfearn, D.P. et al., "Esophageal Temperature Monitoring During Radiofrequency Ablation of Atrial Fibrillation", J Cardiovasc Electrophysiol. vol. 16, pp. 589-593, Jun. 2005.

Sanchez-Quintana, D. M.D. et al., "Anatomic Relations Between the Esophagus and Left Atrium and Relevance for Ablation of Atrial Fibrillation", Circulation, 2005;112:1401-1406.

Tsao, H. M.D. et al., "Anatomic Proximity of the Esophagus to the Coronary Sinus: Implication for Catheter Ablation Within the Coronary Sinus", J Cardiovasc Electrophysiol. vol. 17, pp. 1-4, Apr. 2006.

Wu, T. et al., "Using Left Atrial Esophagus Impression after a Barium Swallow to Determine the Optimal Septal Puncture Site During Percutaneous Balloon Miral Valvuloplasty", Canadian Journal Cardiology, vol. 19, No. 13:1509-1512, Dec. 2003. English Abstract only.

Wu, T. et al., "Using Left Atrial Esophagus Impression after a Barium. Swallow to Determine the Optimal Septal Puncture Site During Percutaneous Balloon Miral Valvuloplasty", Canadian Journal Cardiology, vol. 19, No. 13:1509-1512, Dec. 2003.

European Search Report EP 07250947 dated Jan. 25, 2008.

\* cited by examiner

ESOPHAGUS IMAGING ENHANCEMENT DEVICE

FIELD OF THE INVENTION

The present invention relates generally to medical and therapeutic systems, and particularly to methods and devices for enhancing the imaging quality of organs during therapeutic procedures.

BACKGROUND OF THE INVENTION

Catheter-based cardiac procedures such as cardiac ablation may sometimes cause damage to the esophagus, since sections of the esophagus often pass in close proximity to the left atrium and coronary sinus. The anatomical proximity of the left atrium to the esophagus is described, for example, by Lemola et al., in "Computed Tomographic Analysis of the Anatomy of the Left Atrium and the Esophagus: Implications for Left Atrial Catheter Ablation," Circulation, (110:24), Dec. 14, 2004, pages 3655-60, which is incorporated herein by reference. The proximity of the coronary sinus to the esophagus is described, for example, by Tsao et al., in "Anatomic Proximity of the Esophagus to the Coronary Sinus: Implication for Catheter Ablation Within the Coronary Sinus," to be published in the Journal of Cardiovascular Electrophysiology, (17:4), Apr., 2006, which is incorporated herein by reference.

Some methods and systems are known in the art for enhancing the safety of such procedures. For example, Pollak et al., describe imaging techniques for imaging the esophagus in a report entitled "Novel Imaging Techniques of the Esophagus Enhancing Safety of Left Atrial Ablation," Journal of Cardiovascular Electrophysiology, (16:3), March, 2005, pages 244-248, which is incorporated herein by reference.

The report describes imaging techniques performed during radio-frequency (RF) catheter ablation of atrial fibrillation in the left atrium. According to the report, a mixture of barium cream and gadolinium diglutamate allowed esophageal imaging during magnetic resonance angiography of the left atrium and pulmonary veins. In another technique, barium cream used during computer tomography angiographic imaging of the left atrium and pulmonary veins allowed esophageal imaging. The esophagus was also imaged with an electroanatomic mapping system. According to the report, esophageal and left atrial imaging helped to avoid catheter ablation in left atrial tissue overlapping the esophagus.

Wu and Wang describe a method of using left atrial esophagus imaging for a balloon valvuloplasty application in a report entitled "Using Left Atrial Esophagus Impression After a Barium Swallow to Determine the Optimal Septal Puncture Site During Percutaneous Balloon Mitral Valvuloplasty," Canadian Journal of Cardiology, (19:13), December, 2003, pages 1509-1512, which is incorporated herein by reference. The study describes methods for transseptal catheterization for percutaneous balloon mitral valvuloplasty (PBMV) procedures. The left atrial (LA) impression on the esophagus after a barium swallow was used as a reference of LA silhouette to determine the septal puncture site.

SUMMARY OF THE INVENTION

In some medical procedures, such as cardiac ablation, it is desirable to enhance the imaging quality of an organ. For example, when performing ablation in the left atrium, it is desirable to enhance the imaging quality of the esophagus in order to avoid ablating regions of the endocardium adjacent to the esophagus.

Thus, embodiments of the present invention provide devices for enhancing the visualization quality of an organ when imaged by a visualization system. The visualization system may comprise an imaging system, a mapping system, or both. The disclosed devices comprise a structure comprising material that is clearly visible when imaged by the visualization system. The structure is inserted into the organ and self-conforms to an inner surface of the organ, in order to enhance the visualization quality of the surface when using the visualization system.

In some embodiments, position sensors are attached to the device in order to enable position tracking and/or registration of the image of the organ with images from other sources.

There is therefore provided, in accordance with an embodiment of the present invention, a device for enhancing visualization of an esophagus when imaged by a visualization system, the device including:

a structure including material that is clearly visible when imaged by the visualization system, which is arranged, when inserted into the esophagus, to expand so as to conform with an inner surface of the esophagus in order to enhance a visualization quality of the surface when imaged by the visualization system; and a cord attached to the structure, which is arranged to extend out of the esophagus so as to assist a removal of the device from the esophagus.

In an embodiment, the structure includes a metallic wire grid. Additionally or alternatively, the structure may include at least one of a compressible coil, a spring and a flexible mesh tube. In another embodiment, the device includes one or more position sensors, which are attached to the structure and are adapted to provide position coordinates to the visualization system.

There is also provided, in accordance with an embodiment of the present invention, a device for enhancing visualization of an esophagus, the device including:

a structure that is arranged, when inserted into the esophagus, to expand so as to conform with an inner surface of the esophagus; and one or more position sensors, which are attached to the structure and are arranged to produce respective position signals so as to enable a position tracking system to calculate respective positions of the one or more position sensors within the esophagus.

In an embodiment, the position sensors are arranged to sense magnetic fields generated by a magnetic position tracking system and to produce the position signals respectively to the sensed fields. In another embodiment, the position sensors are arranged to sense electrical signals generated by an impedance-based position tracking system and to produce the position signals respectively to the sensed electrical signals.

There is additionally provided, in accordance with an embodiment of the present invention, a device for enhancing visualization of an organ, the device including:

a structure that is arranged, when inserted into the organ, to expand so as to conform with an inner surface of the organ; and one or more position sensors attached to the structure and are arranged to produce respective position signals so as to enable a position tracking system to calculate respective positions of the one or more position sensors within the organ.

There is further provided, in accordance with an embodiment of the present invention, a system for treating a patient, including:

a visualization system, which is arranged to image at least part of a body of a patient; and a marker device including a structure that is arranged, when inserted into an esophagus of the patient, to expand so as to conform with an inner surface of the esophagus in order to enhance a visualization quality of the surface when imaged by the visualization system.

In an embodiment, the mapping system includes at least one of a magnetic position tracking system and an impedance-based position tracking system.

In another embodiment, the visualization system includes an imaging system operative to image the esophagus in addition to the mapping system, and the visualization system is arranged to register the position coordinates of the position sensors with images produced by the imaging system and to jointly display the position coordinates and the images to a physician.

In yet another embodiment, the system includes a catheter, which is adapted to be inserted into a heart of the patient for performing a medical procedure in the heart, and the visualization system is arranged to determine relative positions of the catheter and the esophagus. In still another embodiment, the visualization system is arranged to detect an alert condition related to the procedure responsively to the relative positions and to alert a physician when the alert condition is detected.

There is additionally provided, in accordance with an embodiment of the present invention, a system for treating a patient, including:

a visualization system, which is arranged to image at least part of a body of a patient; and a marker device including a structure including material that is clearly visible when imaged by the visualization system, which is arranged, when inserted into an. organ of the patient, to expand so as to conform with an inner surface of the organ in order to enhance a visualization quality of the surface when imaged by the visualization system.

There is also provided, in accordance with an embodiment of the present invention, a method for treating a patient, including:

inserting into an esophagus of the patient a marker device including a structure that is arranged to expand so as to conform with an inner surface of the esophagus;

forming an image of a thorax of the patient in which the structure in the esophagus indicates a locus of the esophagus in the image; and performing a medical procedure in the thorax of the patient using the image.

In an embodiment, performing the medical procedure includes at least one of preplanning the procedure and verifying a result of the procedure using the image.

There is further provided, in accordance with an embodiment of the present invention, a method for treating a patient, including:

inserting into an organ of the patient a marker device including a structure that is arranged to expand so as to conform with an inner surface of the organ;

forming an image of at least part of a body of the patient in which the structure in the organ indicates a locus of the organ in the image; and performing a medical procedure in the at least part of the body of the patient using the image.

The present invention will be more fully understood from the following detailed description of the embodiments thereof, taken together with the drawings in which:

DETAILED DESCRIPTION OF EMBODIMENTS

Figure 1:
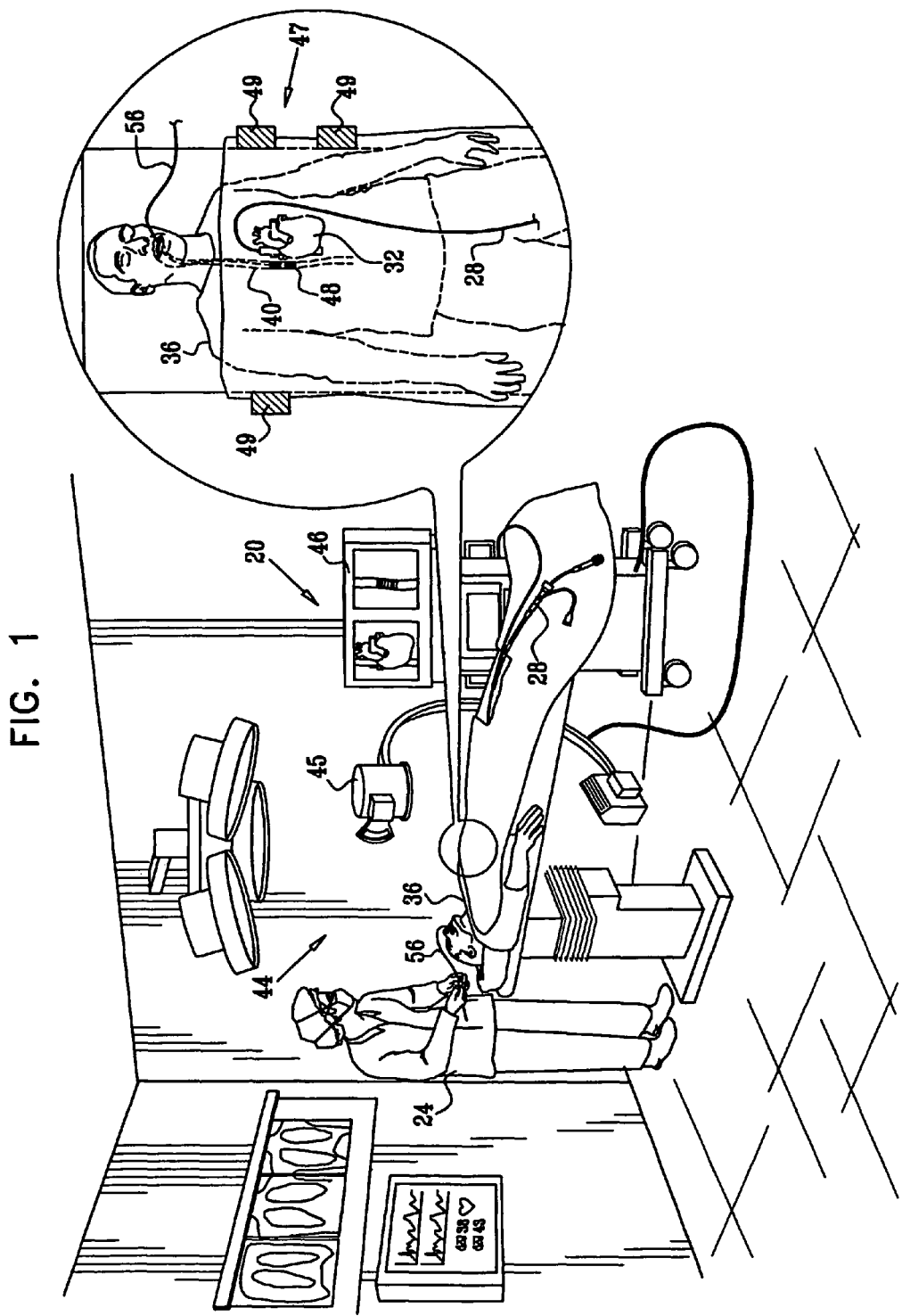
FIG. 1 is a schematic, pictorial illustration of a system for performing cardiac ablation, in accordance with an embodiment of the present invention.

FIG. 1 is a, schematic, pictorial illustration of a system 20 for performing cardiac ablation, in accordance with an embodiment of the present invention. A physician 24 inserts a catheter 28 into a heart 32 of a patient 36 in order to perform a cardiac ablation procedure. Catheter 28 typically comprises an ablation electrode, which applies concentrated RF energy to selected spots on the endocardium (the inner surface of the heart), as is known in the art.

In some cases, parts of an esophagus 40 of the patient may overlap, or be adjacent to, parts of heart 32, and in particular the posterior part of the left atrium and the coronary sinus. Because of this proximity, the ablation procedure may cause thermal damage to the esophagus, sometimes resulting in its perforation.

In order to prevent damage from being caused to the esophagus, a visualization system 44 provides the physician with an image of at least part of the patient's body, typically comprising the heart and the parts of the esophagus that are in close proximity to the heart. The visualization system displays images showing the positions of the cardiac chamber in which the ablation procedure takes place, the catheter performing the procedure, and the region of the esophagus adjacent to the heart. Using these images, the physician is able to plan and perform the ablation procedure while avoiding areas of the endocardium that are in close proximity to the esophagus.

In some embodiments, system 44 comprises an imaging system 45. The imaging system uses a certain imaging modality, in which body parts and features are imaged responsively to differences in their material composition and/or their chemical or physical properties. For example, system 4may comprise a fluoroscopic imaging system in which body parts of the patient are irradiated with x-rays. The x-ray radiation transmitted through the body is received by detectors and used to reconstruct images of the irradiated body parts. Other examples of imaging modalities comprise ultrasonic, computerized tomography (CT) and magnetic resonance imaging (MRI) systems. Typically, imaging modalities also enable tracking the position of catheter 28, by virtue of its different material composition and physical properties.

Additionally or alternatively, system 44 comprises a mapping system 47, which uses a certain mapping modality in which the system tracks the positions of dedicated intrabody sensors. For example, a sensor can be fitted in catheter 28. System 47 then tracks the positions of the sensor in order to map the desired organs and display the current position of the catheter relative to the map. The map may be registered with and superimposed on images captured by imaging system 45.

For example, mapping system 47 may comprise a magnetic position tracking system, which tracks position sensors, such as coils, fitted into catheters and/or other intrabody objects. Some systems and methods for magnetic position tracking are described, for example, in PCT Patent Publication WO 96/05768, U.S. Pat. Nos. 5,391,199, 5,443,489, 6,690,963, 6,239,724, 6,618,612 and 6,332,089, and U.S. Patent Application Publications 2002/006545 A1, 2003/0120150 A1 and 2004/0068178 A1, whose disclosures are all incorporated herein by reference.

Referring to the exemplary configuration of FIG. 1, magnetic position tracking system 47 comprises field-generating coils 49, which generate magnetic fields in a working volume that includes the relevant parts of the heart and esophagus. System 47 tracks sensors fitted into catheter 28 and into a device inserted into the esophagus, as will be explained below. The sensors sense the magnetic fields generated by coils 49 and produce respective position tracking signals, which are indicative of the sensor positions. By tracking the positions of the sensors, system 47 can present the position of the catheter with respect to the esophagus and heart to the physician.

As another example of a mapping modality, system 47 may comprise an impedance-based position tracking system, which tracks the position of an electrode attached to an intrabody object. The electrode senses an electrical signal transmitted through the body tissue from externally attached transducers. Exemplary impedance-based tracking systems are described in U.S. Pat. Nos. 5,983,126, 6,456,864, and 5,944,022, and in U.S. patent application Ser. No. 11/030,934 filed on Jan. 7, 2005, whose disclosures are incorporated herein by reference.

Alternatively or additionally, visualization system 44 may use any other suitable imaging and/or mapping modality known in the art, or a combination of such modalities. System 44 comprises a display 46, which presents the imaged heart, esophagus and catheter to the physician.

In order to enhance the visualization quality of the esophagus by visualization system 44, an esophagus marker device 48 is inserted into the region of the esophagus adjacent to the heart. In principle, device 48 is constructed so as to enable it to self-conform to the inner surface of the esophagus. Device 48 is constructed, as described in detail hereinbelow, so that the device is clearly visible when imaged by the visualization system. Thus, once inserted and self-aligned with the surface of the esophagus, device 48 marks the surface of the esophagus so that the surface is displayed clearly and accurately by the visualization system.

An exemplary embodiment of device 48 is described in detail with reference to FIGS. 2A and 2B below. As will be explained, the characteristics of marker device 48 should match the modality used, so that the marker device will be imaged clearly by visualization system 44.

Figure 2A:
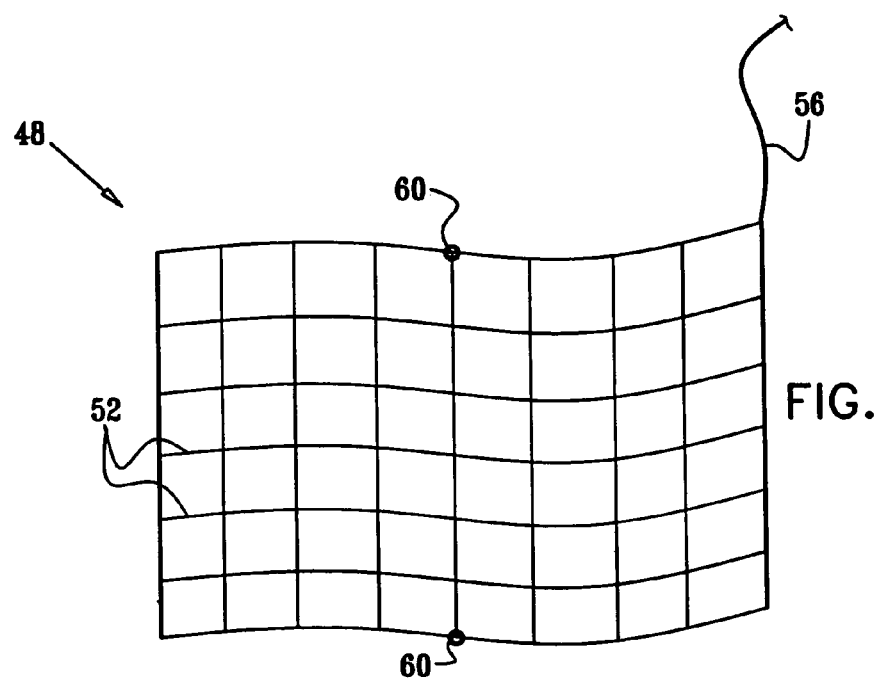
FIGS. 2A and 2B are schematic, pictorial illustrations of a device for visualizing an esophagus, in accordance with an embodiment of the present invention.
Figure 2B:
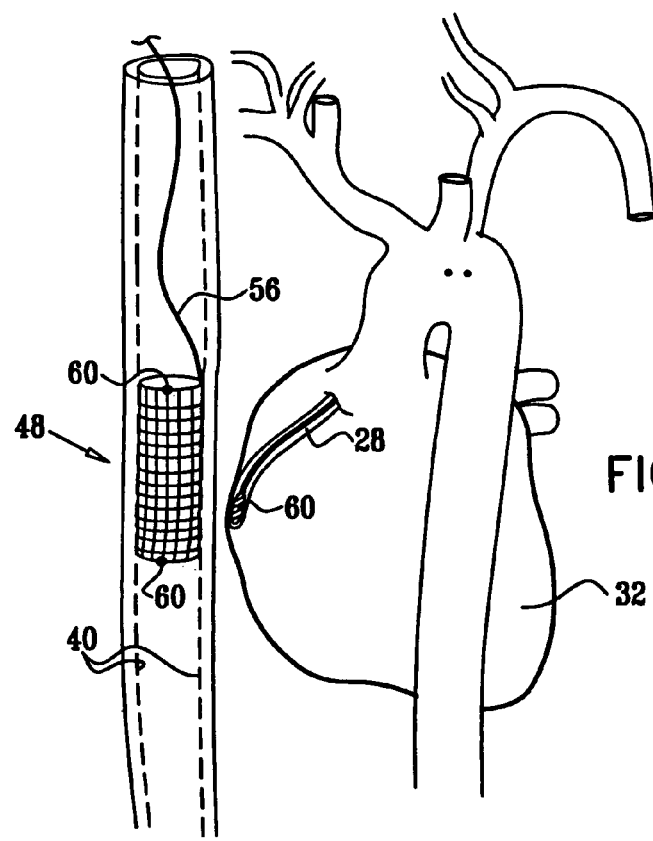

FIGS. 2A and 2B are schematic, pictorial illustrations of marker device 48, in accordance with an embodiment of the present invention. In this embodiment, device 48 comprises a resilient grid 52 of material that is clearly visible when imaged by imaging system 45. For example, when imaging system 4 comprises a fluoroscopic imaging system, grid 52 may comprise flexible metallic wires. As another example, echogenic polymer coating can be used to enhance the visualization under intra-cardiac ultrasound guidance. In alternative embodiments, device 48 may comprise any suitable structure, comprising material that is clearly imaged by imaging system 45, which self-conforms to the inner surface of the esophagus. For example, device 48 may comprise a compressible coil or spring or a flexible mesh tube (stent). FIG. 2A shows device 48 with grid 52 shown fully flattened in order to demonstrate its structure. In some embodiments, grid 52 is folded, rolled, wound, contracted or otherwise tightened in order to enable it to be inserted into the esophagus of the patient. Device 48 is inserted through the patient's mouth into the esophagus. When reaching the desired region of the esophagus (e.g., the region next to the heart), the device is allowed to self-extract and self-conform to the inner surface of the esophagus.

In some embodiments, device 48 is initially held in its tightened form using an external sheath (not shown). After inserting the device, the external sheath is gradually pulled back and the device is allowed to self-extract and self-conform to the inner surface of the esophagus. In these embodiments, device 48 can be removed by pulling it back into the external sheath. In an alternative embodiment, device 48 can be expanded to fit the inner surface of the esophagus by inflating a balloon inserted into the tightened device, and subsequently removed by deflation. The balloon may also be filled with hot water, thereby causing device 48 to shrink back into its tightened form, enabling its safe retrieval.

In some embodiments, device 48 comprises a cord 56, which is connected at one end to grid 52. When device 48 is inserted into the esophagus, cord 52 extends out of the patient's mouth so as to allow device 48 to be pulled out after the procedure is completed. In some cases, cord 56 can also be used to provide an estimate of the depth of device 48 in the esophagus.

FIG. 2B shows device 48 after it was inserted and has self-aligned with the inner surface of esophagus 40. It can be seen that device 48 follows the contours of the esophagus closely, thereby effectively marking the exact shape and location of the esophagus in a manner that is clearly imaged by imaging system 45.

In some embodiments, when visualization system 44 comprises a mapping system 47, one or more sensors 60 may be attached to grid 52 of device 48. For example, when system 44 comprises a magnetic position-tracking system, sensors 60 comprise position sensors, such as field sensing coils, that sense the magnetic fields generated by mapping system 47. The position sensors translate the sensed fields to-uses respective position signals that are transmitted back to system 47. Mapping system 47 the position signals to calculate the positions of the position sensors. As another example, when mapping system 47 comprises an impedance-based tracking system, sensors 60 comprise suitable potential-sensing electrodes.

Sensors 60 may be connected to mapping system 47 using wires (not shown) traveling along cord 56. A similar sensor 60 is fitted in the distal end of catheter 28. FIG. 2B shows catheter 28 inserted into the heart and located next to the endocardium, in close proximity to esophagus 40. By tracking the positions of the sensors, mapping system 47 is able to calculate and display the coordinates of catheter 28 with respect to several points of reference in device 48. The physician can use this relative display to avoid ablating spots on the endocardium that are too close to the esophagus. Although FIGS. 2A and 2B show two sensors 60 attached to device 48, any number of sensors can be attached to grid 52.

When mapping system 47 comprises a magnetic position tracking system, sensors 60 may also be used to register the image of the grid with a three-dimensional map of the heart generated by imaging system 45. In some embodiments, the sensor measurements can be used to register the image of device 48 with another 3-D image (either a real-time image or a pre-acquired image) of the heart.

Figure 3:
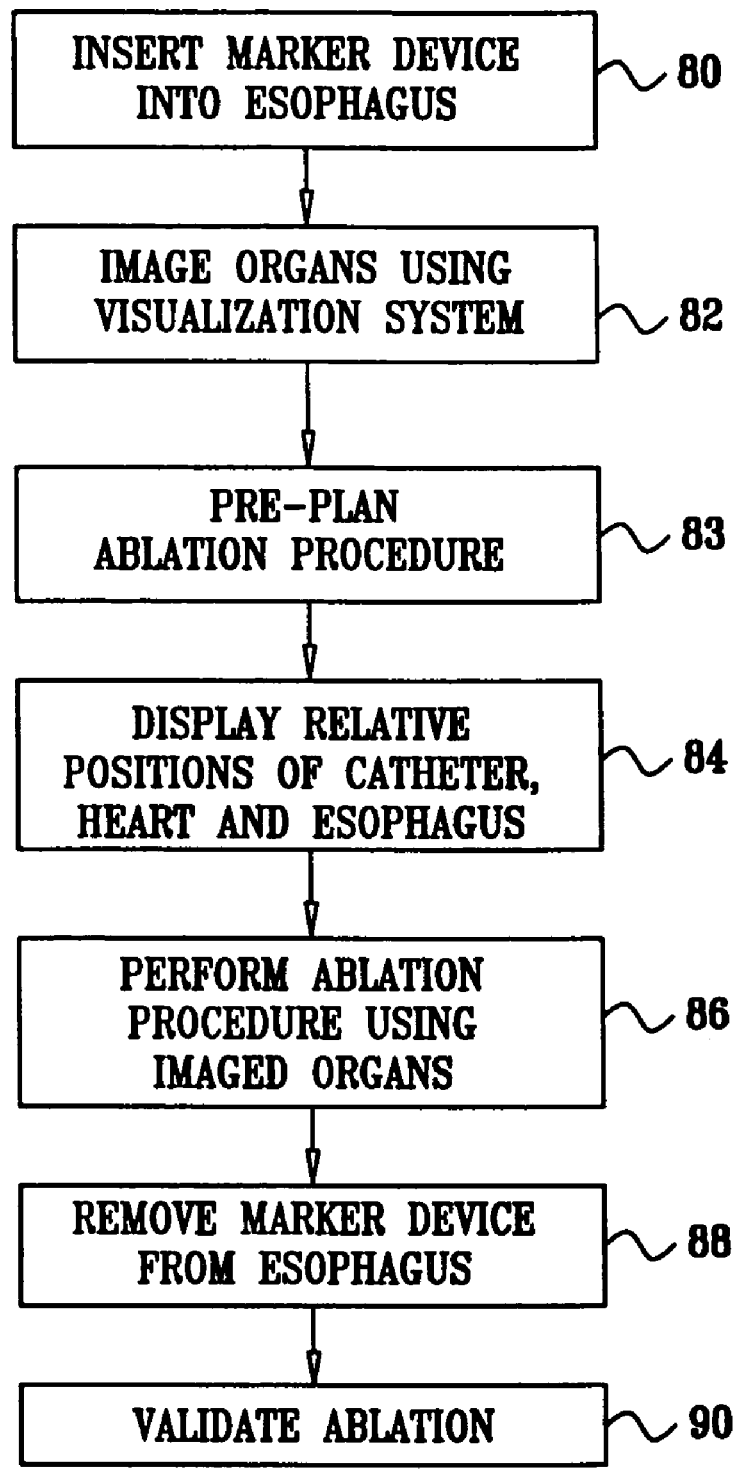
FIG. 3 is a flow chart that schematically illustrates a method for performing cardiac ablation while visualizing the esophagus, in accordance with an embodiment of the present invention.

FIG. 3. is a flow chart that schematically illustrates a method for performing cardiac ablation while visualizing the esophagus, in accordance with an embodiment of the present invention. The method begins with the physician inserting esophagus marker device 48 into esophagus 40 of patient 36, at an insertion step 80. After inserting the device to the desired region of the esophagus, the device is allowed to self-extract and self-conform to the inner surface of the esophagus.

The physician uses visualization system 44 to image at least part of the patient's body, at an imaging step 82. Typically, the imaged volume comprises the heart and the parts of the esophagus adjacent to the heart. The visualization system displays esophagus 40, whose visualization quality has been enhanced by device 48. System 44 also displays heart 24 and catheter 28 inserted into it.

In some embodiments, the physician may preplan the ablation procedure using the visualized organs, at a preplanning step 83. Aspects of ablation preplanning are described, for example, in U.S. patent application Ser. No. 11/195,050, filed Aug. 2, 2005, which is assigned to the assignee of the present patent application and whose disclosure is incorporated herein by reference.

Assisted by the display of visualization system 44, the physician performs the cardiac ablation procedure, at an ablation step 86. The images of the heart, esophagus and catheter enables the physician to avoid spots on the endocardium that are dangerously close to the esophagus, thus increasing the safety of the procedure. Aspects of online guidance of ablation procedures are described, for example, in U.S. Patent Application Publication 2004/0078036 A1, whose disclosure is incorporated herein by reference, and in U.S. patent application Ser. No. 11/195,123, filed Aug. 2, 2005, which is assigned to the assignee of the present patent application and whose disclosure is incorporated herein by reference.

In some embodiments, the visualization system may automatically alert the physician in real-time when the catheter location is considered dangerous, i.e., too close to the esophagus. When system 44 comprises a position tracking system, for example, an alert condition can be detected responsively to position-tracking measurements of the sensor 60 in catheter 28 relative to the sensors 60 attached to device 48. The alert may comprise any suitable means to attract the physician's attention, such as an audible alarm, a change of color or other visual indication on display 46.

After the ablation procedure is completed, the physician removes device 48 from the esophagus, through the patient's mouth, at a removal step 88. In some embodiments, the physician may assess and/or validate the results of the ablation procedure, at a validation step 90. Exemplary assessment and validation methods are described in U.S. Patent Application Publication 2004/0147920 A1, whose disclosure is incorporated herein by reference.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. A system for treating a patient, comprising:
a marker device comprising a structure configurable to form a hollow tubular shape having a proximal end and a distal end, the structure having an opening in the proximal end and the distal end, that is arranged, when inserted into an esophagus of the patient, to expand so as to conform with an inner surface of the esophagus in order to enhance a visualization quality of the surface when imaged by a visualization system, the marker device comprising one or more first position sensors attached to the structure;

one or more second position sensors adapted to be arranged in the patient at a location which is separate from the location of the marker device;

the visualization system arranged to image at least the esophagus and the location of the one or more second position sensors, and a catheter for treating the patient by performing a medical procedure, wherein the catheter is configured to be inserted into a heart of the patient for performing the medical procedure in the heart.

2. The system according to claim 1, wherein the structure comprises material that is clearly visible when imaged by the visualization system.

3. The system according to claim 1, wherein the visualization system comprises an imaging system operative to image the esophagus, and wherein the structure comprises at least one of a metallic wire grid, a compressible coil, a spring and a flexible mesh tube.

4. The system according to claim 1, wherein the visualization system comprises a mapping system operative to track respective positions of the one or more first and second position sensors so as to calculate position coordinates of the one or more first and second position sensors.

5. The system according to claim 4, wherein the mapping system comprises at least one of a magnetic position tracking system and an impedance-based position tracking system.

6. The system according to claim 4, wherein the visualization system comprises an imaging system operative to image the esophagus in addition to the mapping system, and wherein the visualization system is arranged to register the position coordinates of the one or more first and second position sensors will images produced by the imaging system and to jointly display the position coordinates and the images to a physician.

7. The system according to claim 1, wherein the visualization system is arranged to determine relative positions of the catheter and the esophagus.

8. The system according to claim 7, wherein the visualization system is arranged to detect an alert condition related to the procedure responsively to the relative positions and to alert a physician when the alert condition is detected.

9. The system according to claim 1, wherein the marker device comprises a cord attached to the structure, which is arranged to extend out of the esophagus so as to assist a removal of the marker device from the esophagus.

10. The system according to claim 1, wherein the length of the marker device remains the same once it is expanded in the esophagus.

11. A system for treating a patient, comprising:
a marker device comprising a structure configurable to form a hollow tubular shape having a proximal end and a distal end, the structure having an opening in the proximal end and the distal end, comprising material that is clearly visible when imaged by a visualization system, which is arranged, when inserted into an organ of the patient, to expand so as to conform with an inner surface of the organ in order to enhance a visualization quality of the surface when imaged by the visualization system, the device comprising one or more first position sensors attached to the structure;

one or more second position sensors adapted to be arranged in the patient at a location which is separate from the location of the marker device;

the visualization system arranged to image at least the esophagus and the location of the one or more second position sensors, and a catheter for treating the patient by performing a medical procedure, wherein the catheter is configured to be inserted into a heart of the patient for performing the medical procedure in the heart.

12. The system according to claim 11, wherein the length of the marker device remains the same once it is expanded in the organ.

13. A method for treating a patient, comprising:
inserting into an esophagus of the patient a marker device comprising a structure configurable to form a hollow tubular shape having a proximal end and a distal end, the structure having an opening in the proximal end and the distal end, that is arranged to expand so as to conform with an inner surface of the esophagus in order to enhance a visualization quality of the surface when imaged by a visualization system;
arranging one or more position sensors in the patient at a location which is separate from the location of the marker device;
forming an image of a thorax of the patient and the one or more position sensors in which the structure in the esophagus indicates a locus of the esophagus in the image; and
performing a medical procedure in the thorax of the patient using the image, wherein performing the medical procedure comprises inserting a catheter into a heart of the patient for performing the medical procedure in the heart.

14. The method according to claim 13, wherein forming the image comprises visualizing the thorax using a visualization system, and wherein the structure comprises material that is clearly visible when imaged by the visualization system so as to indicate the locus of the esophagus in the image.

15. The method according to claim 13, wherein the visualization system comprises an imaging system operative to image the esophagus, and wherein the structure comprises at least one of a metallic wire grid, a compressible coil, a spring and a flexible mesh tube.

16. The method according to claim 13, wherein the marker device comprises one or more position sensors attached to the structure and arranged to produce respective position signals so as to enable a position tracking system to calculate respective positions of the one or more position sensors within the esophagus, and wherein forming the image comprises tracking and displaying the respective positions of the one or more position sensors using the position tracking system.

17. The method according to claim 16, wherein the position tracking system comprises at least one of a magnetic position tracking system and an impedance-based position tracking system.

18. The method according to claim 16, wherein forming the image comprises registering the respective position coordinates of the one or more position sensors with an image produced by an imaging system and jointly displaying the position coordinates and the image produced by the imaging system to a physician.

19. The method according to claim 16, wherein the catheter comprises a position sensor, and wherein forming the image comprises tracking and displaying a relative position of the catheter with respect to the esophagus using the position tracking system.

20. The method according to claim 19, wherein performing the medical procedure comprises detecting an alert condition related to the procedure responsively to the relative position of the catheter and alerting a physician when the alert condition is detected.

21. The method according to claim 13, wherein performing the medical procedure comprises at least one of preplanning the procedure and verifying a result of the procedure using the image.

22. The method according to claim 13, wherein the marker device comprises a cord attached to the structure, wherein inserting the marker device comprises extending the cord out of the esophagus, and comprising removing the marker device from the esophagus using the cord following the procedure.

23. The method according to claim 13, wherein the length of the marker device remains the same once it is expanded in the esophagus.

24. A method for treating a patient, comprising:
inserting into an organ of the patient a marker device comprising a structure configurable to form a hollow tubular shape having a proximal end and a distal end, the structure having an opening in the proximal end and the distal end, that is arranged to expand so as to conform with an inner surface of the organ in order to enhance a visualization quality of the surface when imaged by a visualization system;
arranging one or more position sensors in the patient at a location which is separate from the location of the marker device;
forming an image of at least part of a body of the patient and the one or more position sensors in which the structure in the organ indicates a locus of the organ in the image; and
performing a medical procedure in the at least part of the body of the patient using the image, wherein performing the medical procedure comprises inserting a catheter into a heart of the patient for performing the medical procedure in the heart.

25. The method according to claim 24, wherein forming the image comprises visualizing the at least part of the body using a visualization system, and wherein the structure comprises material that is clearly visible when imaged by the visualization system so as to indicate the locus of the organ in the image.

26. The method according to claim 24, wherein the length of the marker device remains the same once it is expanded in the organ.

* * * * *